US009527825B2

(12) United States Patent
Bucher et al.

(10) Patent No.: US 9,527,825 B2
(45) Date of Patent: Dec. 27, 2016

(54) PURIFICATION OF TAXANES (71) Applicant: Phyton Holdings, LLC, San Antonio, TX (US)

(72) Inventors: Brian A. Bucher, Boston, MA (US); Edward M. Desimone, III, Indianapolis, IN (US); Roland R. Franke, Gloucester, MA (US); Rex T. Gallagher, Hampton, MA (US); Barry J. Hand, Acton, MA (US); Christopher D. Howe, Beverly, MA (US); James H. Johnson, Edenton, NC (US); John S. Juchum, Kingston, NH (US); Marc A. Plante, Middleton, MA (US); T. G. Sambandam, Uxbridge, MA (US); Dong S. Yang, Quincy, MA (US)

(73) Assignee: Phyton Holdings, LLC, San Antonio, TX (US)

( * ) Notice: Subject to any disclaimer, the term of this patent is extended or adjusted under 35 U.S.C. 154(b) by 0 days.

(21) Appl. No.: 15/053,793

(22) Filed: Feb. 25, 2016

(65) Prior Publication Data

US 2016/0176837 A1    Jun. 23, 2016

Related U.S. Application Data (63) Continuation of application No. 14/188,416, filed on Feb. 24, 2014, now Pat. No. 9,303,004, which is a continuation of application No. 12/705,247, filed on Feb. 12, 2010, now Pat. No. 8,703,982, which is a continuation of application No. 11/764,362, filed on Jun. 18, 2007, now Pat. No. 7,897,796, which is a continuation of application No. 10/549,490, filed as application No. PCT/US2004/008055 on Mar. 17, 2004, now abandoned, which is a continuation of application No. 10/664,539, filed on Sep. 18, 2003, now Pat. No. 6,956,123.

(60) Provisional application No. 60/456,478, filed on Mar. 21, 2003, provisional application No. 60/455,377, filed on Mar. 17, 2003.

(51) Int. Cl.
*C07D 305/14* (2006.01)
*C07D 407/12* (2006.01)

(52) U.S. Cl.
CPC ........... *C07D 305/14* (2013.01); *C07D 407/12* (2013.01)

(58) Field of Classification Search
CPC .................................................. C07D 305/14
USPC ........................................................ 549/510
See application file for complete search history.

(56) References Cited

U.S. PATENT DOCUMENTS

| | | | |
|---|---|---|---|
| 4,814,470 A | 3/1989 | Colin et al. ................... | 514/449 |
| 5,085,779 A | 2/1992 | Crane et al. .................. | 210/635 |
| 5,092,992 A | 3/1992 | Crane et al. ............... | 210/198.2 |
| 5,279,949 A | 1/1994 | Nair .............................. | 435/123 |
| 5,281,727 A | 1/1994 | Carver et al. ................. | 549/510 |
| 5,475,120 A | 12/1995 | Rao ............................... | 549/510 |
| 5,478,736 A | 12/1995 | Nair .............................. | 435/123 |
| 5,670,673 A | 9/1997 | Rao ............................... | 549/510 |
| 5,969,165 A | 10/1999 | Liu ............................... | 549/510 |
| 6,008,385 A | 12/1999 | Durand et al. ................ | 549/510 |
| 6,022,985 A | 2/2000 | Authelin et al. .............. | 549/510 |
| 6,184,395 B1 | 2/2001 | Singh et al. .................. | 549/510 |
| 6,197,980 B1 | 3/2001 | Durand et al. ................ | 549/510 |
| 6,221,153 B1 | 4/2001 | Castor et al. ................... | 117/11 |
| 6,229,027 B1 | 5/2001 | Liu ............................... | 549/510 |
| 6,495,705 B2 | 12/2002 | Chander et al. .............. | 549/510 |
| 6,541,508 B2 | 4/2003 | Ekwuribe et al. ............ | 514/449 |
| 6,838,569 B2 | 1/2005 | Sharma et al. ............... | 549/510 |
| 6,858,644 B2 | 2/2005 | Benigni et al. .............. | 514/449 |
| 6,881,852 B2 | 4/2005 | Sharma et al. ............... | 549/510 |
| 6,891,050 B2 | 5/2005 | Sharma et al. ............... | 549/510 |
| 6,956,123 B2 | 10/2005 | Johnson et al. .............. | 549/510 |
| 7,176,325 B2 | 2/2007 | Johnson et al. .............. | 549/510 |
| 7,220,872 B2 | 5/2007 | Johnson et al. .............. | 549/511 |
| 7,332,617 B2 | 2/2008 | Li et al. ........................ | 549/510 |
| 7,662,980 B2 | 2/2010 | Lia et al. ...................... | 549/510 |
| 8,703,982 B2 | 4/2014 | Bucher et al. ................ | 549/510 |
| 2002/0052403 A1 | 5/2002 | Holton ......................... | 514/449 |
| 2002/0137927 A1 | 9/2002 | Thottathil et al. ............. | 540/35 |
| 2003/0013899 A1 | 1/2003 | Chang et al. ................ | 549/510 |
| 2004/0116720 A1 | 6/2004 | Sharma et al. ............... | 549/510 |

FOREIGN PATENT DOCUMENTS

| | | |
|---|---|---|
| CA | 2119261 | 12/1993 |
| CA | 2149021 | 12/1993 |
| CA | 2129288 | 8/1994 |
| CA | 2170661 | 2/1996 |
| CA | 2354486 | 1/2003 |
| EP | 1 193 252 | 4/2002 |
| JP | 2002-44904 | 2/2002 |
| JP | 11-89826 | 11/2003 |
| WO | WO 03/087078 | 10/2003 |
| WO | WO 03/087079 | 10/2003 |

(Continued)

OTHER PUBLICATIONS

2001/2002 Phenomenex Catalog, p. 382.
Nail and Stickelmeyer, "Preparation and Characterization of the Drug," In: Injectable Disperesed Systems, Formulation, Processing, and Performance (Drugs and the Pharmaceutical Sciences), Diane J. Burgress, Ed., Taylor & Francis: Boca Raton, FL, vol. 149, pp. 180-181, 2005.
Office Communication, issued in U.S. Appl. No. 11/764,362, dated Apr. 15, 2009.

(Continued)

*Primary Examiner* — Taofiq A Solola
(74) *Attorney, Agent, or Firm* — Norton Rose Fulbright US LLP (57) ABSTRACT

Disclosed is a method of crystallizing docetaxel comprising combining docetaxel and at least one solubilizing solvent to obtain a solution, wherein the solubilizing solvent is methylene chloride and adding an anti-solvent to the solution to obtain a crystalline docetaxel, wherein the anti-solvent is water.

10 Claims, 8 Drawing Sheets

(56) References Cited

FOREIGN PATENT DOCUMENTS

WO    WO 2005/075427    8/2005

OTHER PUBLICATIONS

Office Communication, issued in U.S. Appl. No. 11/764,362, dated Sep. 5, 2008.
Wu et al., "Preparative separation of taxol in normal-and-reversed-phase-operations," Journal of Chromatography, pp. 223-241, 1995.
Young and Porter, "The Hydrocarbons," In: General Chemsitry: A First Course, Prentice-Hall, Inc.: New York, pp. 537-538, 1950.
Zaske et al., "Docetaxel: Solid state characterization by X-ray powder diffraction and thermogravimetry," J. Phys. IV France, 11:Pr10-221-Pr10-226, 2001.
Lee et al., "Preparation and characterization of solvent induced dihydrated, anhydrous, and amorphous paclitaxel," Bull. Korean Chem. Soc., 22(8):925-928, 2001.
Office Communication, issued in European Patent Application No. 04 757 522.0, dated Jan. 18, 2011.
Extended European Search Report issued in European Patent Application No. EP 11002035.1, dated Jul. 22, 2011.
Office Communication issued in Canadian Patent Application No. 2,733,837, dated May 28, 2012.
Office Action issued in European Divisional Application No. 11002035.1, dated Jul. 10, 2012.
Sanofi-Aventis, "Taxotere Injection(docetaxel hydrate) approved in Japan for the treatment of prostate cancer", Press release, Sep. 1, 2008, pp. 1-4.
Siddiqui et al., "Determination of residual solvents in docetaxel by headspace gas chromatography", *Arab Jol Chem*, 1-6, 2013.

FIGURE 1

C-2'-O-Benzoyl Migration Chemistry

FIGURE 2

Primary Amine Conversion Chemistry

Taxane Molecules

10-Deacetyltaxol A

10-Deacetyltaxol B

10-Deacetyltaxol C

7-Xylosyltaxol A

7-Xylosyl, 10-deacetyltaxol A

Docetaxel

7-Xylosyl, 10-deacetyltaxol C

FIGURE 6

Primary Taxanes

*Comparison of Retention of Times of Taxane Standards on Differing Media*

| Taxane | C-18[5] | | Silica[2] | | PEI[3] | | DEAM[4] | |
|---|---|---|---|---|---|---|---|---|
| | Rt[7] | Rel Rt[6] | Rt[7] | Rel Rt[6] | Rt[7] | Rel Rt[6] | Rt[7] | Rel Rt[6] |
| 10-Deacetyl-Baccatin III | 3.3 | 0.16 | 27.9 | 2.53 | 11.7 | 0.92 | 9.7 | 0.73 |
| Baccatin III | 6.3 | 0.31 | 11.1 | 1.01 | 5.5 | 0.44 | 5.6 | 0.42 |
| 10-Deacetyl-Taxol | 12.5 | 0.61 | 26.8 | 2.43 | 55.2 | 4.36 | 41.6 | 3.13 |
| Cephalomannine | 18.1 | 0.88 | 12.7 | 1.15 | 8.9 | 0.71 | 8.9 | 0.67 |
| 10-Deacetyl, 7-epi-Taxol | 19.8 | 0.97 | 7.6 | 0.69 | 12.0 | 0.95 | 10.9 | 0.82 |
| Paclitaxel | 20.5 | 1.00 | 11.0 | 1.00 | 12.6 | 1.00 | 13.3 | 1.00 |
| Taxol C | 25.3 | 1.23 | 11.1 | 1.00 | 7.8 | 0.62 | 7.6 | 0.57 |
| N-Methyl-Taxol | 25.9 | 1.26 | 14.9 | 1.35 | 6.2 | 0.49 | 5.7 | 0.43 |
| 7-epi-Taxol | 29.4 | 1.43 | 6.2 | 0.56 | 8.1 | 0.64 | 8.3 | 0.62 |
| N-Methyl-Taxol C | 36.4 | 1.78 | 11.7 | 1.06 | 4.9 | 0.39 | 4.7 | 0.35 |
| 2'-Benzoyl-Taxol | 42.2 | 2.06 | 5.9 | 0.54 | 4.3 | 0.34 | 4.3 | 0.32 |
| iso-Cephalomannine | --- | --- | --- | --- | --- | --- | 11.9 | 0.90 |

PURIFICATION OF TAXANES

CROSS REFERENCE TO RELATED APPLICATIONS

This application is a continuation of U.S. application Ser. No. 14/188,416, filed Feb. 24, 2014, which is a continuation of U.S. application Ser. No. 12/705,247 filed Feb. 12, 2010 (which issued as U.S. Pat. No. 8,703,982, on Apr. 22, 2014), which is a continuation of U.S. application Ser. No. 11/764,362, filed Jun. 18, 2007 (which issued as U.S. Pat. No. 7,897,796 on Mar. 1, 2011), which is a continuation of U.S. application Ser. No. 10/549,490, filed Sep. 15, 2005, which is a 371 National Phase Application of PCT/US2004/008055, filed Mar. 17, 2004, which is a continuation of U.S. application Ser. No. 10/664,539, filed Sep. 18, 2003 (which issued as U.S. Pat. No. 6,956,123 on Oct. 18, 2005), which claims the benefit of U.S. Provisional Application No. 60/456,478, filed Mar. 21, 2003 and U.S. Provisional Application No. 60/455,377, filed Mar. 17, 2003. The contents of all of these applications are incorporated by reference.

FIELD OF THE INVENTION

The present invention relates to a process for separating or isolating one or more taxane compounds from materials containing taxanes, and to the compositions or compounds resulting therefrom. The present invention also relates to a process for purifying a biomass extract comprising one or more taxanes. In one embodiment, the process involves using one or more amino containing material attached to a matrix (e.g., solid matrix), including but not limited to, polyethyleneimine-bonded silica chromatographic resins (PBS resins). These resins facilitate the purification of taxanes in high yield and purity. In one embodiment, the chromatographic resin comprises a non-functionalized and/or non-derivatized polyethyleneimine ("PEI") polymer bonded to silica of various particle sizes or pore sizes. In another embodiment, the polyethyleneimine is methylated to form a diethylaminomethyl-bonded silica ("DEAM"). In one alternative embodiment of the present invention, both DEAM and PEI may be used in normal-phase chromatography under acidic pH.

BACKGROUND OF THE INVENTION

The present invention involves isolating or separating paclitaxel or other taxanes from materials containing one or more taxanes using an amino containing material supported by a solid matrix such as PBS resins. The present invention also involves purifying a biomass extract containing taxanes.

It is well known that various taxanes, e.g., paclitaxel, can be purified by using chromatographic techniques. Chromatographic media such as silica, alumina, alkyl-bonded silica resins such as C18 and C8, and polystyrene divinylbenzene resins have been reported in the literature to be useful for this purpose. However, depending on the nature of the purification process, all of these media have limitations.

It has been discovered that amino containing material attached to a matrix (e.g., PBS resins) may provide superior selectivity and resolution over other conventional chromatographic resins used to isolate and purify taxanes. Therefore, amino containing materials attached to a matrix (e.g., PBS resins) can be utilized to perform separations more efficiently than other resins in the area of taxane purification. For instance, in the literature, the separation of paclitaxel (taxol A) and cephalomannine (taxol B) has been described as difficult. The separation of these compounds is greatly facilitated using one or more PBS resins, as described herein. Also, since PBS resins can be utilized using organic solvents, the resin may be more easily loaded and samples can be applied at higher loading than reverse-phase resins such as C18, C8, and polystyrene divinylbenzene.

PBS resins are primarily used in ion-exchange chromatography applications. Very few taxanes contain an ionizable group such as carboxyclic acid or amine groups and therefore the mode of interaction is not traditional ionic exchange. Unexpectedly, the use of PBS resins provides superior selectivity and resolution in isolating or purifying taxanes. In the present invention, the PBS resins work best when small amounts of an acidic modifier or salt are used in the mobile phase.

In addition, we have discovered that the amino groups of the PEI polymer can be functionalized by alkylation, arylation, or acylation. We have also discovered that PBS resin may be used to perform preparative and analytical separations of taxane compounds. Preparative separations can be carried out in a batch, semi-continuous, or continuous mode. Semi-continuous mode may be in the form of simulated moving bed (SMB) chromatography.

SUMMARY OF THE INVENTION

The present invention involves isolating or separating paclitaxel or other taxanes from materials containing one or more taxanes using an amino containing material attached (e.g., bonded) to a solid matrix, including but not limited to, a polyethyleneimine matrix capable of isolating or separating taxanes, such as polyethyleneimine bonded to silica. Other suitable amino containing materials attached to a matrix (e.g., solid matrix) may include those materials disclosed in U.S. Pat. Nos. 5,085,779 and 5,092,992. Both of these patents are incorporated herein by reference in their entirety.

In one alternative embodiment, the present invention is directed to the use of PEI resins to aid in the separation or purification of various taxanes, including paclitaxel, from compositions containing taxanes. It is believed that the use of these resins for this purpose is both novel and superior over the prior art. The preferred resins include PEI and DEAM.

In one alternative embodiment, the present invention is directed to a method of isolating one or more taxanes, and analogues thereof, from a taxane mixture. The taxane mixture may include a biomass extractor or it may be obtained from semi-synthetic or total synthetic processes. The method comprising the steps of: (a) treating the taxane mixture with an amino containing material attached to a matrix (e.g., PBS resin); (b) eluting one or more taxanes and their analogues from the chromatographic resins; and (c) recovering the one or more taxanes and their analogues in one or more fractions of eluate.

In another alternative embodiment, the present invention is directed to a method of purifying and/or increasing the concentration of taxanes in a taxane containing material, such as a *Taxus* extract, or taxane mixture obtained from semi-synthetic or total synthetic processes, derived from plant material selected from the group of plants known as Yew. The method comprising the steps of: (a) treating the material comprising taxanes and their natural analogues with an amino containing material attached to a matrix (e.g., PBS resin); (b) eluting the taxanes and their analogues from the chromatographic resin; and (c) recovering the taxane and their analogues in one or more fractions of eluate.

The present invention and its advantages will be further understood by reference to the following detailed description and the accompanying drawings.

DETAILED DESCRIPTION OF THE INVENTION

As used herein, an "alkoxy group" means a linear, branched, or cyclic saturated hydrocarbon attached to an oxygen atom. Preferably, an alkoxy group has between one and six carbon atoms. An alkoxy group also refers to substituted alkoxy groups, which may include substituents such as alkanoyloxy groups, alkenyl groups, alkyl groups, alkylsilyl groups, alkylsulfonyl groups, alkylsulfoxy groups, alkylthio groups; alkynyl groups, amino groups such as mono- and dialkylamino groups and mono- and di-arylamino groups, amide groups, aryl groups, arylalkyl groups, carboxy groups, carboxyalkoxy groups, carboxyamide groups, carboxylate groups, haloalkyl groups, halogens, hydroxyl groups, nitrile groups, nitro groups, phosphate groups, siloxy groups, sulfate groups, sulfonamide groups, sulfonyloxy groups, and combinations of these. Preferred examples of alkoxy groups include, among others, methoxy, ethoxy, propoxy, cyclopropoxy, isopropoxy, n-butoxy, isobutoxy, sec-butoxy, tert-butoxy, cyclobutoxy, pentoxy, isopentoxy, neo-pentoxy, cyclopentoxy, hexoxy, and cyclohexoxy.

As used herein, an "alkyl group" means a linear, branched, or cyclic saturated hydrocarbon. Preferably, an alkyl group has between one and six carbon atoms. An alkyl group also refers to substituted alkyl groups, which may include substituents such as alkanoyloxy groups, alkenyl groups, alkyl groups, alkylsilyl groups, alkylsulfonyl groups, alkylsulfoxy groups, alkylthio groups; alkynyl groups, amino groups such as mono- and di-alkylamino groups and mono- and diarylamino groups, amide groups, aryl groups, arylalkyl groups, carboxy groups, carboxyalkoxy groups, carboxyamide groups, carboxylate groups, haloalkyl groups, halogens, hydroxyl groups, nitrile groups, nitro groups, phosphate groups, siloxy groups, sulfate groups, sulfonamide groups, sulfonyloxy groups, and combinations of these. Preferred substituents are alkoxy groups, amino groups such as di-alkylamino groups, di-arylamino groups, carboxylic acid-containing groups, haloalkyl groups, halogens, hydroxyl groups, nitrile groups, nitro groups and sulfuric acid groups. Examples of preferred alkyl groups include, but are not limited to, methyl, ethyl, propyl, isopropyl, cyclopropyl, n-butyl, isobutyl, sec-butyl, tert-butyl, cyclobutyl, pentyl, 1-ethylpropyl, cyclopentyl, hexyl, and cyclohexyl.

As used herein, an "aryl group" means a phenyl group or naphthyl group, which is optionally substituted. Examples of substituents on aryl groups including, but are not limited to, alkanoyloxy groups, alkenyl groups, alkoxy groups, alkylsilyl groups, alkylsulfonyl groups, alkylsulfoxy groups, alkylthio groups; allynyl groups, amino groups such as mono- and di-alkylamino groups and mono- and di-arylamino groups, amide groups, aryl groups, arylalkyl groups, carboxy groups, carboxyalkoxy groups, carboxyamide groups, carboxylate groups, haloalkyl groups, halogens, hydroxyl groups, nitrile groups, nitro groups, phosphate groups, siloxy groups, sulfate groups, sulfonamide groups, sulfonyloxy groups, and combinations of these. Preferred substituents are alkoxy groups, alkyl groups, amino groups such as dialkylamino groups and diarylamino groups, carboxylic acid-containing groups, haloalkyl groups, halogens, hydroxyl groups, nitrile groups, nitro groups and sulfonic acid groups.

As used herein, an "arylalkyl group" means an aryl group attached to an alkyl group. An example of an arylalkyl group is a benzyl group.

Figure 6:
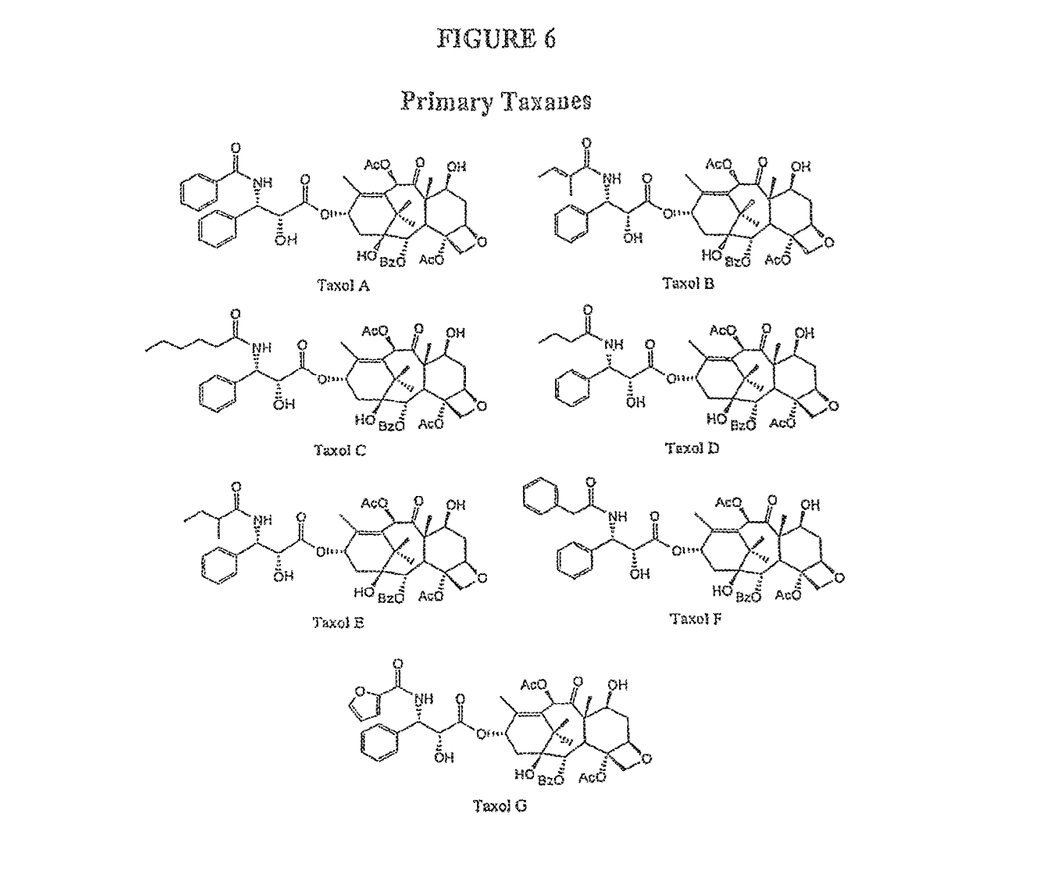
FIG. 6 shows non-limiting, exemplary compounds ("primary taxanes").
Figure 7:
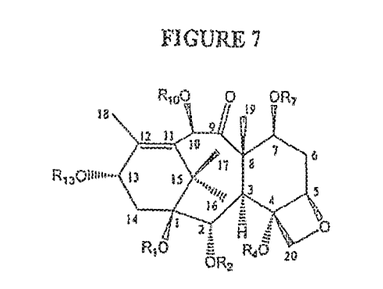
FIGS. 7-9 show non-limiting, exemplary taxane molecules.
Figure 8:
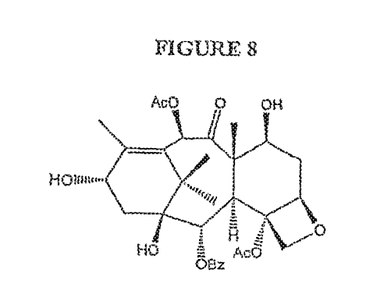
Figure 9:
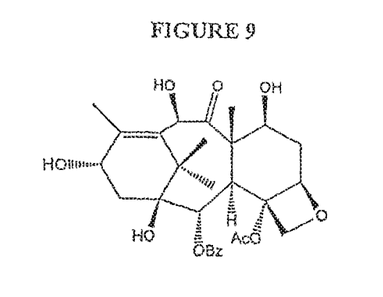

As used herein, a "basic baccatin III structure" means a compound having the formula as shown in FIG. 6, where each of R1, R2, R4, R7, R10 and R13 independently is hydrogen, an alkyl group, an acyl group, an aryl group, an arylalkyl group, a vinyl group, an ether group, an ester group, a glycoside group, an oxo group, or a hydroxyl protecting group. Included within the definition of a basic baccatin III structure is baccatin III, which has the formula as shown in FIG. 7, and 10-deacetylbaccatin III, which has the formula as shown in FIG. 8, where Ac is an acetyl or acetate group (CH3C(0)-), and Bz is a benzoyl group (PhC(0)- or $C_6H_5C(0)$-).

As used herein, an "ester group" means a linear, branched, or cyclic substituent having an ester functionality, i.e., —C(0)-OR. Examples of ester groups include acyl groups such as actyl and benzoyl, which are bound to a hydroxyl group.

As used herein, an "ether group" means a linear, branched, or cyclic substituent having an ether functionality, i.e., —C—O—C—. An example of an ether group includes, but is not limited to, $HOCH_2CH_2OC(CH_2OH)H$—.

As used herein, a "glycoside group" or a "glycosyl group" means any of a number of sugar derivatives that contain a non-sugar group bonded to an oxygen or nitrogen atom and that on hydrolysis yield a sugar such as glucose. An example of a preferred gylcosyl group is xylosyl.

As used herein, a "halogen" means fluorine, chlorine, bromine, and/or iodine.

As used herein, a "heterocyclic group" is a saturated, unsaturated, or aromatic cyclic compound that contains at least one atom other than carbon, e.g., oxygen, nitrogen, or sulfur, in a ring. Examples of heterocyclic groups include furyls such as 2-furan, morpholino, piperadino, piperazhno, N-methylpiperaziuo, pyrrollyl, pyridyl, and thiophenz.

As used herein, an "oxo-group" means a substituent derived from the oxidation of a glycoside group such as a xyloside as described in U.S. Pat. No. 5,356,928.

Figure 5:
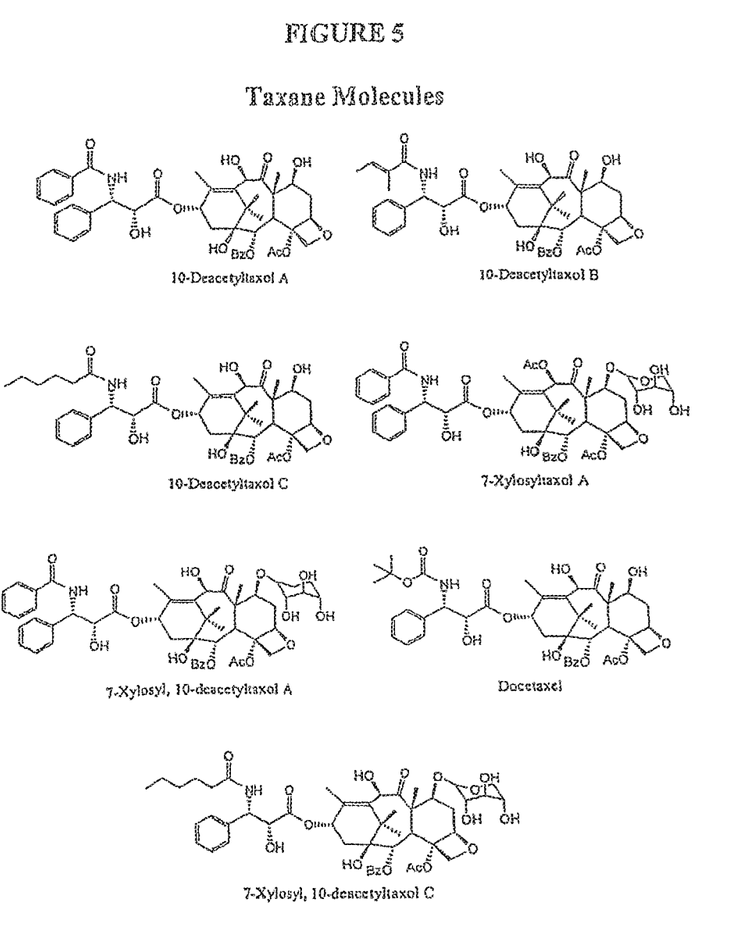
FIG. 5 shows non-limiting taxine molecules.

As used herein, "taxane or taxane molecule" includes but is not limited to a molecule that contains a basic baccatin III structure with a (2R,3 S)—$C_6H_5CH(Rx)CH(OH)C(0)$- group forming an ester with the hydroxyl group located at the C-13 position of the basic baccatin III structure. The group represented by Rx can be an amino group, a salt of an amino group (e.g., an ammonium salt), an amino group which is protected with an amino protecting group, or a substituent which may be converted into an amino group. Various isomers, homologues, and analogues of the basic baccatin III structure, and of the (2R,3 S)—$C_6H_5CH(Rx)$ $CH(OH)C(0)$- group also are included in the definition of a taxane molecule. Also, a 10-deacetylbaccatin III structure is contemplated within the scope of a taxane molecule. Included within the definition of a taxane or taxane molecule include, but are not limited to, primary taxanes, for example taxol A (paclitaxel), taxol B (cephalomannine), taxol C, taxol D, taxol E, taxol F, and taxol G. Further, the definition of a taxane or taxane molecule includes docetaxel (TAXOTERE™). (See, e.g., FIGS. 5-6).

As used herein, a "vinyl group" means a linear or branched substituent having a carbon-carbon double bond. Examples of vinyl groups include, but are not limited to, 1-methyl-1-propenyl ($CH_3CH$=$(CH_3)$—), and 2-methyl-l-propenyl (($CH312C$=$CH$—).

Yew is a name ascribed to a number of trees which are *Taxus* species; *Taxus* being the plain genus in the family Taxaceae. Originally isolated from the bark of the Pacific yew (*Taxus brevifolia*) collected from Washington State, beginning in 1962, taxol was subsequently reported as occurring in two other *Taxus* species, including *Taxus baccata,* (European yew) and *Taxus cuspidate* (Japanese yew), in 1971. Following intensive investigations, taxol was further reported to occur in a number of other *Taxus* species and cultivars. These include, but are not limited to: *Taxus globosa* (Mexican yew), *Taxus floridana* (Florida yew), *Taxus canadensis* (Canadian yew), *Taxus wallichiana* (Himalayan yew), *Taxus yunnanensis, Taxus chinensis,* and also a number of ornamental hybrids, such as *Taxus media* cultivars, e.g.: *T. media* 'Densiformis', *T. media* 'Hicksii', *T. media* 'Brownii', *T. media* 'Dark Green Spreader', *T. media* 'Runyan', *T. media* 'Wardii', *T. media* 'Tautonii', *T. euspidata* 'Capitata', etc. In the present invention, the *Taxus* extract or a semi-synthetic reaction mixture may be derived from any *Taxus* species, including but not limited to the species and cultivars described above. Other *Taxus* species for use in the present invention are identified in: Chadwick, L. C. and Keen, R. A. May 1986, "A study of the Genus *Taxus*", Res. Bull. 1086, Ohio Agricultural Research and Development Center; Appendino, G. 1995, "The Phytochemistry of the Yew Tree": Phytochemistry, Natural Products Reports 12(4): 349-360; Convention On International Trade in Endangered Species of Wild Fauna and Flora: Eleventh mooting of the Plants Committee, LangKawi (Malaysia), 3-7 Sep. 2001, Document PC1 DOC. 22-p. 1, United States of America; and Greer, Schutzki, R. E., Fernandez, A. and Hancock, T. F. October/December 1993. "Electrophoretic Characterization of *Taxus Cultivars*": HortTechnology, 3(4): 430-433. Each of these references are incorporated herein by reference in their entirety.

It has now surprisingly been found that taxane compounds, including paclitaxel and paclitaxol analogs and congeners thereof can be isolated and purified from *Taxus* species in high yields by a normal phase liquid chromatography column packed with a PBS resin. By the subject method, a large number of analogues of paclitaxel can be isolated from natural biomass extracts, and materials obtained from semi-synthetic or total synthetic processes.

The starting material for this invention may be a plant material selected from the group of plants commonly referred to its yew trees. The most suitable plants of this group are species of *Taxus*. Among *Taxus* species, *Taxus*× *media* cultivars are particularly preferred. For example, preferred cultivars include, but are not limited to, *T. media* 'Hicksii' or *T. media* 'Dark Green Spreader'. While it is convenient to use certain parts of the yew tree in this invention, taxol and its natural analogues can be extracted from the whole plant or from separated parts such as wood, stems, roots, leaves (needles), seeds, or any combination thereof. The material to be extracted can be either fresh or dried. Preferably, the bark or the needles are used. Further, the method of this invention can be used to purify taxanes from grown plant cells, or culture supernatants obtained by using in vitro culture technology. Additionally, the method is applicable to the separation and purification of taxanes from mixtures treated by chromatographic techniques, or mixtures that have not been treated by such techniques. The method can be further applied to the separation and purification of taxanes obtained from semi-synthesis or total synthesis procedures.

In one aspect of this invention, an amino containing material attached to a matrix (e.g., silica) is used to separate or isolate one or more taxane compounds from mixtures containing taxanes. Such substances to be separated or purified include, but are not limited to, taxol A, B, C, D, E, F, G, Docetaxel, Nonataxel. Examples of such amino containing materials attached to a matrix include, but are not limited to, PBS resins. These resins are typically used in ion-exchange applications, and therefore would not be expected to be useful for separating neutral molecules, such as taxanes which generally contain no ionizable groups. The selectivity and resolution of the separation of taxane mixtures is surprisingly enhanced by using, for example, PBS resins. The PBS resins, for example, are more easily loaded to higher levels than, for example, reverse-phase resins such as C18, C8 and polystyrene divinylbenzene. PBS resins, for example, are also advantageously used with organic solvents.

PBS resins may be derived from polyethyleneimine polymer bound to silica of various pore sizes rind/or particle sizes. The silica having an average pore size ranging from 60-300 Angstrom Units. Preferably, the silica has an average pore size of about 100 to 300 Angstrom units, more preferably about 120 angstrom units. Also, the silica may have an average particle size ranging from about 0.25 to about 500 microns. Preferably, the silica has an average particle size from about 10-120 microns, more preferably about 20 to 60, most preferably about 40.

A suitable PBS resin of the present invention may include DEAM. This resin may be purchased from J. T. Baker, CAS Reg. No. Product Codes: 7317, 7471, 7472, 7473, under the name "BAKERBOND™. DEAM Chromatography Packing." Another suitable PBS resin may include PEI. This resin may also be purchased from J. T. Baker, CAS Reg. No.: 126850-07-5, Product Codes: 7134, 7180. 7264, 7368, 7476 and 8179, under the name "Polyethyleneimine Bonded Silica Gel."

In one alternative embodiment of the present invention, the amino containing material attached to a matrix (e.g., PBS resin) may be non-derivatized, such as, for example, PEI. The chromatographic resins of the present invention may include but are not limited to derivatized PBS resins in which the primary and/or secondary amino groups of the polyethyleneimine moiety are reacted with a reactive moiety. The PBS resins of the present invention may be represented by the generalized formula:

Generalized Structure of PBS Resins:

Silica Suface
PEI: R = H
DEAM: R = CH₃

The above structure is for illustrative, non-limiting purposes only. The structure of the PBS resin may take on many other branching patterns or comprise single or multiple sites of attachment to the surface of the silica particles. Also, the R groups may include, but are not limited to, an H group, methyl group, an acyl group, alkyl group, aryl group, arylalkyl group, sulfonyl group, or any combination thereof.

The amino groups of the PEI polymer may be functionalized by alkylation, arylation, or acylation, or other means. Functionalizing the amino group may lead to a resin with increased selectivity, resolution, or other desired properties. For example, DEAM is a specific example of a functionalized PEI.

The resins of the present invention may be used to isolate or purify taxanes from a taxane mixture, including but not limited to, a biomass extract, such as a *Taxus* extract. In one alternative embodiment, the present invention may be used to isolate or purify taxanes from taxane mixtures (e.g., biomass extracts) produced by solvent partitioning, centrifugation, filtration, precipitation, or any combination thereof. The resins of the present invention may also be used to isolate and/or purify taxanes from a naturally derived taxane containing mixture, wherein the taxanes were not formed from a synthetic or semi-synthetic process. Further, the resins of the present invention may be used to isolate or purify taxanes from mixtures comprising taxanes obtained from semi-synthetic or total synthetic processes.

It is well known that various forms of chromatography such as silica, alumina, C8, C18, polystyrene divinylbenzene, and others are useful in purifying taxol A and other taxanes from *Taxus* extracts. Chromatography may be supplemented by other methods known to those skilled in the art, such as solvent partitioning and crystallization. PBS resins may be used in conjunction with these other techniques to simplify the purification of taxol A and other taxanes from *Taxus* extracts. For example, we have discovered that PBS resins may be particularly effective in separating taxol A from taxol B, N-methyl taxanes, taxane cinnamates, and others. PBS resins may also be used to separate a related group of taxanes, such as primary taxanes (see FIG. 6) from other taxanes found in *Taxus* extracts. PBS resins may be used to separate taxanes from undesirable elements, thereby increasing the taxane concentration in a mixture.

In one alternative embodiment, the starting material may comprise plant material selected from the group of plants commonly referred to as Yew. The must suitable plants of this group are species of *Taxus*. Starting material for use in the present invention may include, but are not limited to: (1) any material comprising one or more taxanes prepared from procedures other than semi-synthesis or total synthesis procedures; (2) any material comprising one or more taxanes prepared from chromatography; (3) any material comprising one or more taxanes not prepared from chromatography; (4) any material comprising one or more taxanes prepared by solvent partitioning, centrifugation, filtration, precipitation, or any combination thereof; (5) any material comprising one or more taxanes from *Taxus* plants; or (6) any material comprising one or more taxanes from one or more *Taxus* plants wherein the taxanes are not derived solely from *Taxus brevifolia*. The starting material may include any material comprising one or more taxanes prepared by any combination of the parameters set forth above. Methods of preparing taxane containing materials (e.g., biomass extracts or semi-synthetic or total synthetic reaction mixtures) are known in the art.

In another alternative embodiment, the present invention is directed to a method of isolating one or more taxanes from a taxane containing mixture, the method comprising, the steps of: (a) treating the mixture with a PBS resin; wherein the one or more taxanes are derived from one or more *Taxus* plants, wherein the one or more taxanes are not derived solely from *Taxus brevifolia;* (b) eluting the one or more taxanes from the PBS resin with an eluant; and (c) recovering the eluted one or more taxanes.

In another embodiment, the present invention is directed to a method of isolating one or more taxanes from a taxane containing mixture, the method comprising the steps of: (a) treating the mixture with a PBS resin; wherein the mixture comprises less than 25% or greater than 40% by weight of primary taxanes; (b) eluting the one or more taxanes from the PBS resin; and (c) recovering the eluted one or more taxanes.

In another embodiment, the present invention is directed to a method of isolating one or more taxanes, the method comprising the steps of: (a) treating a taxane containing mixture with a PBS resin; wherein the mixture comprises from about 25% to 40% by weight of primary taxanes; wherein the one or more taxanes are not derived solely from

*Taxus brevifolia;* (b) eluting the one or more taxanes from the PBS resin; and (c) recovering the eluted one or more taxanes.

In one alternative embodiment of the present invention, the starting material may comprise less than about 25% or greater than about 40% by weight of primary taxanes, including but not limited to taxol A, B, C, D, E, F or G. The remaining materials in the extract may comprise other compounds, including but not limited to impurities. Other suitable amounts of primary taxanes in the starting material may include from about 0.5% to 1%; 1% to 10%; 10% to 15%; 15% to 20%; 20% to 25%; 25% to 30% or 30% to 35%, or 35% to 40%. Other amounts may also include about 40% to 50%; 50% to 60%; 60% to 70%; 70% to 80%; 80% to 90% or 90% to 100%.

In another alternative embodiment, the biomass extract is derived from a *Taxus* plant. In yet another alternative embodiment, the biomass extract is derived from any *Taxus* plant, excluding *Taxus brevifolia*. In yet another alternative embodiment, the biomass extract is derived from any *Taxus* plant, excluding *Taxus brevifolia*, and comprises from about 25% to about 40% by weight of primary taxanes, including but not limited to taxol A, B, C, D, E, F or G.

In another embodiment, the present invention is directed to a method of purifying one or more taxanes compounds from a biomass extract. wherein the biomass extract is derived from one or more *Taxus* plants. In one embodiment, the biomass extract is from one or more *Taxus* plants, excluding *Taxus brevifolia*. In another embodiment, the biomass extract comprises less than 25% or greater than 40% by weight primary taxanes. In yet another embodiment, the biomass extract comprises from about 25% to about 40%, primary taxanes, wherein the biomass extract is derived from one or more *Taxus* plants, excluding *Taxus brevifolia*.

In addition, in one alternative embodiment, the biomass extract may comprise isobutyl alcohol in an amount less than about 50%, 40%, 30% or 20%, preferably less that 10%, more preferably less that 5%, most preferably less than 3%, 2%, 1%, 0.5%, or 0.25%.

The process of the present invention may increase the purity of the biomass extract by about 10% to 20%; 20% to 30%; 30% to 40%; 40% to 50%; 50% to 60%; 60% to 70%; 70% to 80%; 80% to 90%; 90% to 100%; 100% to 110%; 110% to 120%; 120% to 130%; 130% to 140%; 140% to 150%; 150% to 200%; 200% to 250%; 250% to 300%; 300% to 350%; 350% to 400%; 400% to 450%; 450% to 500%; 500% to 550%; 550% to 600%; 600% to 650%; 650% to 700%; 700% to 750%; 750% to 800%: 800% to 850%; 850% to 900%; 900% to 950%; 950% to 1000%. As used herein, the term purity means the weight percent of one or more taxane compounds present in a dried form of the material or biomass extract.

Figure 10:
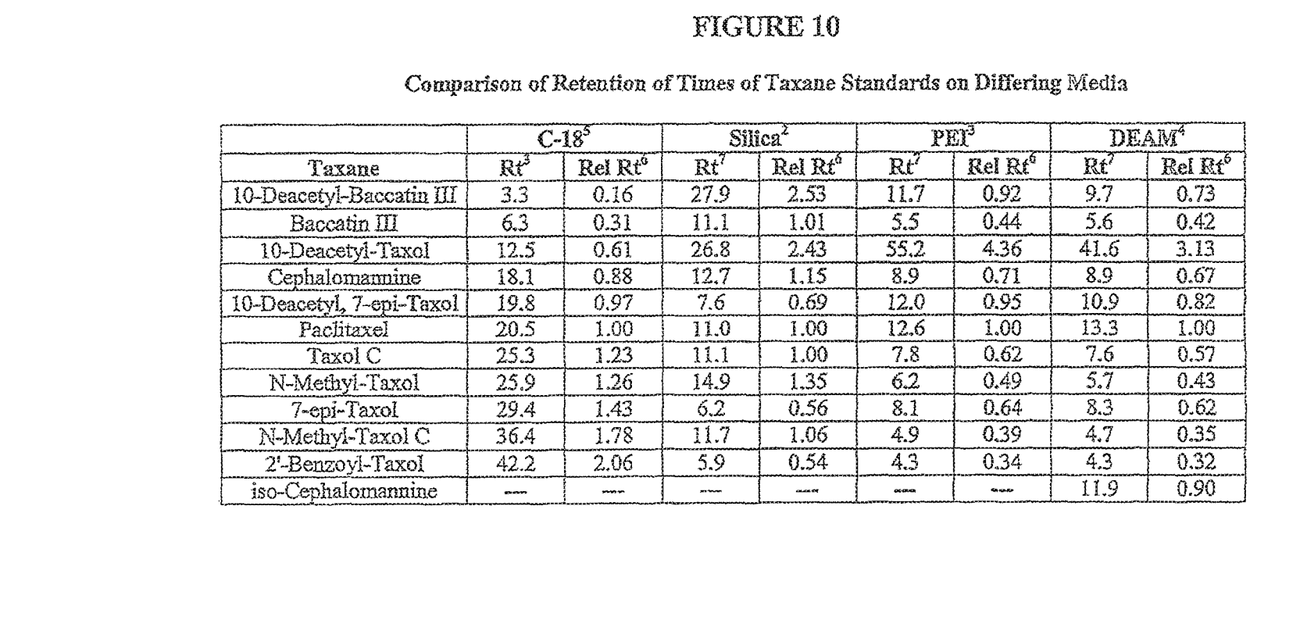
FIG. 10 shows comparison of retention times and taxane standards on various media.

The resin of the present invention may be used to purify one or more taxanes from a taxane mixture obtained, in whole or in part, from a semi-synthetic or total synthetic process. In one alternative embodiment, the resin of the present invention may be used to purity semi-synthetic taxol A or other semi-synthetic taxanes from a crude reaction mixture. Because most synthetic reactions generate by-products or unreacted starting materials that in many cases are structurally closely related to the desired product, the process of purifying such products is very important. For example, PBS resins have been shown to enhance and amplify the purification of semi-synthetic taxol A produced from processes described herein from many related impurities and structurally related compounds as shown in FIG. 10, for example.

Figure 1:
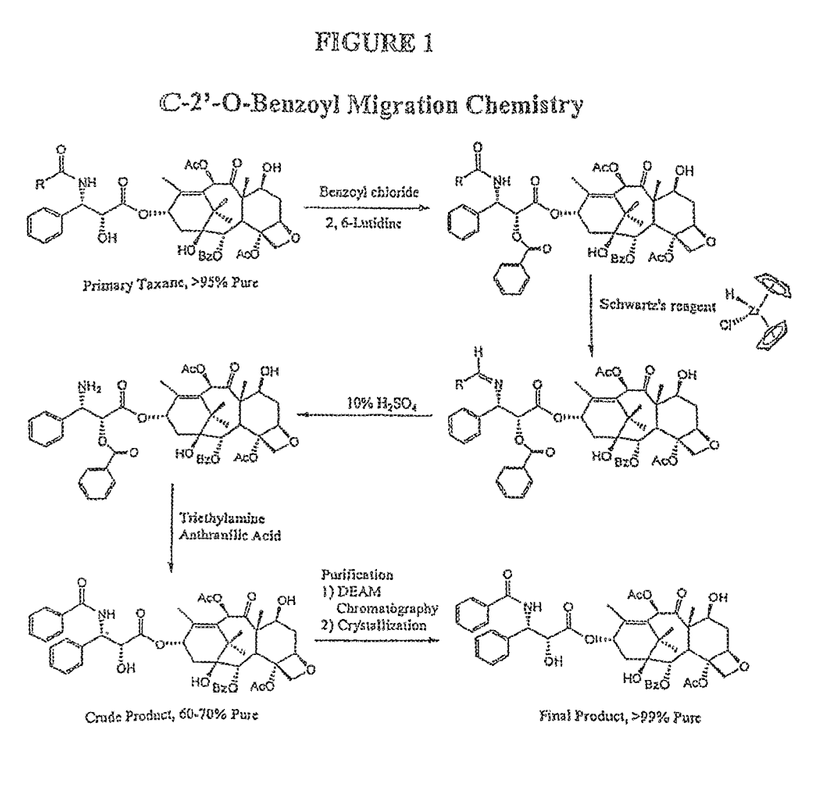
FIG. 1 shows an exemplary chemical reaction scheme using a chromatographic resin of the present invention.
Figure 2:
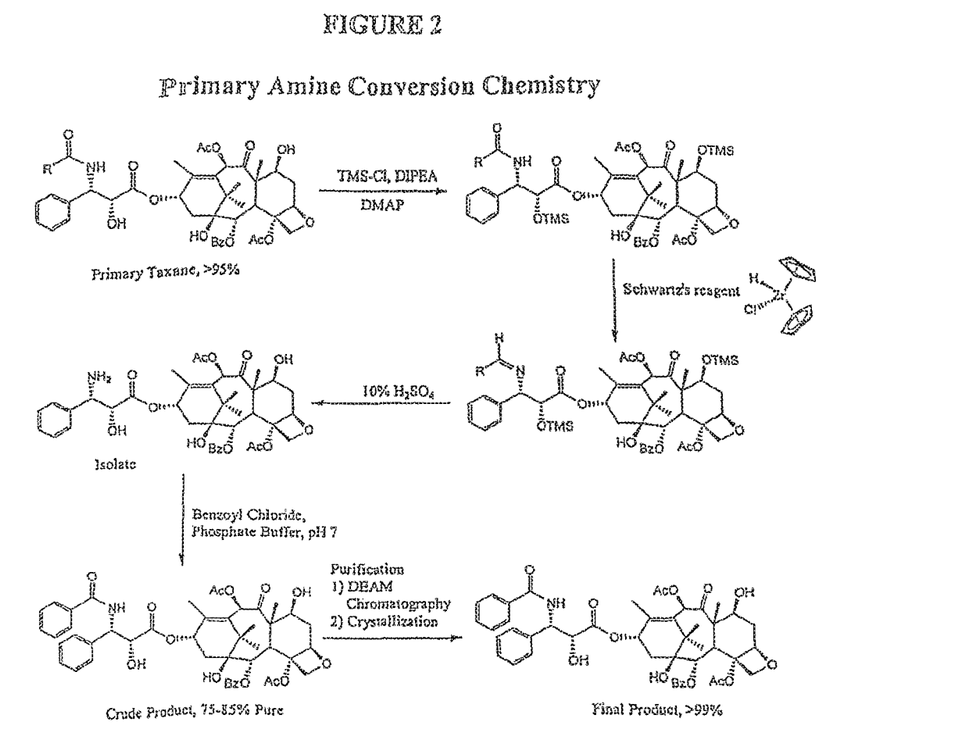
FIG. 2 shows an exemplary chemical reaction scheme using a chromatographic resin of the present invention.

In one alternative embodiment, the present invention involves purifying one or more taxane compounds from materials prepared from a semi-synthesis or total synthesis process. FIGS. 1 and 2 show an exemplary, non-limiting semi-synthesis processes utilizing the resins or the present invention. The processes are described in Serial Appl. No. PCT/US03/10556 entitled "Conversion of Taxane Molecules and Serial Appl. No. PCT/JUS03/24666" Methods and Compositions for Converting Taxane Amides to Paclitaxel or Other Taxanes" filed Aug. 4, 2003. Each of above-mentioned application is incorporated herein by reference in its entirety.

In one alternative embodiment, such materials comprising less than about 10% by weight of C-2' benzoyl primary taxanes, preferably less than about 5%, more preferably less than about 3%, most preferably less than about 1%. In another alternative embodiment, the taxane containing materials comprising less than about 9%, 8%, 7%, 6%, 4%, 2%, 1%, 0.5%, 0.1%, or 0.01%. The taxane impurities include, but are not limited to, the C-2' bonzoates of taxol A, B, C, D, E, F, or G. The taxane impurities may also include less than about 10%, 9%, 8%, 7%, 6%, 5%, 4%, 3%, 2%, 1%, or 0.5% of the C-2' benzoates of taxol B, C, D, E, F or G. As used herein, the term weight percent means the percentage of one or more compounds present in a dried solid form of such material.

In one alternate embodiment, the present invention is directed to a method of isolating one or more taxanes from material comprising taxane compounds obtained from a semi-synthesis or total synthesis process, the method comprising the steps of: (a) treating the material with a PBS resin; wherein molecules used as reactants in the semi-synthetic or -total synthetic process are nor derived solely from *Taxus brevifolia;* (b) eluting the one or more taxanes from the PBS resin; and (c) recovering the eluted one or more taxanes.

In another embodiment, the present invention is directed to a method of isolating one or more taxanes from material comprising taxane compounds obtained from a semi-synthesis or total synthesis process: (a) treating the material with a PBS resin; wherein the material comprises less than from about 8% to 3% by weight of 2' benzoates of taxol A, B, C, D, E, F or G, combined; (b) eluting the one or more taxanes; and (c) recovering the eluted one or more taxanes. In another embodiment, the present invention is directed to a method of isolating one or more taxanes from material comprising taxane compounds obtained from a process that excludes the step of benzoylating the C-2' hydroxyl group of the taxane molecules.

In another embodiment, the present invention is directed to a method of isolating one or more taxanes from material comprising taxane compounds obtained from a semi-synthesis or total synthesis process, the method comprising the steps of: (a) treating the material with a PBS resin; wherein the material comprises less than 0.5% by weight of 2' benzoates of taxol B, C, D, E, F or G, combined; (b) eluting the one or more taxanes; and (c) recovering the eluted one or more taxanes.

In another alternative embodiment, the present invention is directed to a method of preparing a taxane mixture. The method comprising the steps of treating a material comprising one or more taxanes obtained by a semi-synthetic or total synthetic process with a PBS resin. The taxanes or other compounds used in the semi-synthetic process are derived from one or more *Taxus* plants, or one or more *Taxus* plants excluding *Taxus brevifolia*. In another embodiment the taxane containing material comprising less than 3% by weight of 2' benzoates of taxol A, B, C, D, E, F or G. In another embodiment, the taxane containing material comprising less than 0.5% of the C-2' benzoates of taxol A, B, C, D, E, F or G.

In another alternative embodiment, materials to be processed by the present invention may comprise benzoic anhydride, benzoic acid and benzoyl chloride, preferably in amounts less than 10%, preferably less than 5%, more preferably less than 1% and most preferably less than 0.3%.

With respect to materials obtained from semi-synthesis or total synthesis procedures, when these materials are processed by the present invention, the desired product(s) resulting therefrom may have a purity of at least 70%, preferably at least about 80%, more preferably at least about 90%, most preferably at least about 91%, 92%, 93%, 94%, 95%, 96%, 97%, 98%, 99% or 100%.

In another alternative embodiment, the material to be processed by the present invention may comprise taxane impurities having a molecular weight of approximately 1104 and/or an oxetane ring-opened taxanes having a molecular weights of approximately 871, among others.

The process of the present invention may increase the purity of a particular taxane in the material by about 10% to 20%; 20%, to 30%; 30% to 40%; 40% to 50%; 50% to 60%; 60% to 70%; 70% to 80%; 80% to 90%; 90% to 100%; 100% to 110%; 110% to 120%; 120% to 130%; 130% to 140%; 140% to 150%; 150% to 200%; 200% to 250%; 250% to 300%; 300% to 350%; 350% to 400%; 400% to 450%; 450% to 500%; 500% to 550%; 550% to 600%; 600% to 650%; 650% to 700%; 700% to 750%; 750% to 800%; 800% to 850%; 850% to 900%; 900% to 950%; 950% to 1000%. As used herein, the term purity means the weight percent of one or more taxane compounds present in a dried form of the material.

One embodiment of the present invention involves preparative-scale separation of taxane compounds, including paclitaxel, using a PBS resin. A preparative separation may be carried out in batch, semi-continuous, or continuous mode. Semi-continuous and continuous modes may be in the form of simulated moving bed (SMB) chromatography.

In another embodiment, the present invention includes the use of PBS resins to perform a separation by liquid chromatography. In one such embodiment, a small amount of an acid or salt modifier is used in the mobile phase of the liquid chromatographic separation. The acid or salt modifiers used in the mobile phase may include, but are not limited to, acetic acid, formic acid, ammonium acetate or ammonium formate.

PBS resins may run in a normal-phase mode and exhibit unique selectivity for taxanes. For standard types of chromatography, both on C-18 and on silica, other taxanes can elute before and after paclitaxel. In normal-phase chromatography on PBS resins, most other structurally similar taxanes elute before paclitaxel allowing simplicity in preparative separations. Of the most common taxanes, 10-deacetyltaxol elutes after paclitaxel on PBS resins. Fortuitously, the greatly extended retention time of 10-deacetyl-taxol allows for easy separation on preparative systems. This is important because 10-deacetyltaxol can be a significant by-product in semi-synthetic preparations and is also commonly found in natural extracts of *Taxus* spp.

FIG. 10 shows comparison of retention times and taxane standards on various media. In FIG. 10, Footnote 1 represents Phenomenex™ Synergi™ Hydro-RP, 4 mm (250×4.6 mm) HPLC column: acetonitrile/water gradient elution (40% to 60% ACN over 45 minutes) at 1.5 ml/min. Footnote 2 represents Amicon Si-100-10sp (250×4.6 mm) HPLC column: Isocratic elution, 60% ethyl acetate/40% hexanes and 1.0 ml/min. Footnote 3 represents J. T. Baker™ Wide-Pore PEI, 5 microns (250×4.6 mm) HPCC column: Isocritic elution, 80% ethyl acetate/20% hexanes (with 0.5% Acetic Acid) at 1.0 ml/min. Footnote 4 represents J. T. Baker™ Wide Pore DEAM, 5 micro (250×4.6 mm) HPCC column: Isocratic elution, ethyl acetate (with 0.5% acetic acid) at 1.0 ml/min. Footnote 5 represents retention times from a single injection of a mixture of taxane standards. Footnote 6 represents retention times relative to paclitaxel. Footnote 7 represents times on an average of three injections of a single taxane standard.

PET bonded resins exhibit a similar selectivity for taxanes, but some taxanes still elute in close proximity to paclitaxel (e.g., 10-deacetyl-7-epi-taxol, see FIG. 10). Chemically modified forms of PEI, such as DEAM, retain the same pattern of selectivity and exhibit greater separation of paclitaxel from its closest eluting taxanes.

The PBS resins have a high affinity for taxanes. As seen in FIG. 10, a mixture: of about 60% ethyl acetate and about 40% hexanes is sufficient to elute paclitaxel in a reasonable time from silica. In some situations, PEI requires a stronger mix of solvents: e.g., about 79.75% ethyl acetate, 19.75% hexanes and 0.5% acetic acid. DEAM's affinity for paclitaxel was stronger than PEI's, requiring a mixture of about 99.5% ethyl acetate and about 0.5% acetic acid as its mobile-phase. The stronger solvent systems used with PEI and DEAM dissolve taxanes to a greater extent thus allowing for higher loading.

In some variations, polyethyleneimine-bonded silica resins are used to separate various taxanes, including paclitaxel, from mixtures of taxanes, such as *Taxus* extracts, or semi-synthetic or total synthetic taxane reaction mixtures. Suitable methods and compositions for producing semi-synthetic taxane mixtures comprising paclitaxel were described in Application Ser. No. 60/401,191 (the '191 application), filed Aug. 4, 2002; PCT/US03/10557, filed Apr. 5, 2003; Provisional Application entitled "Method and Compositions for Preparing a Pharmaceutical Compound (e.g., Paclitaxel or other Taxanes) Using a Benzoylating Agent Essentially Free of Ring Chlorination", U.S. Ser. Appl. No. 60/444,847 filed Feb. 4, 2003. Each of these applications is incorporated herein by reference in its entirety.

In one alternative embodiment, the process of the present invention comprises one or more of the following steps: (i) packing a column with all appropriate amount of PBS resin; (ii) equilibrating the column with an organic solvent, preferably acetone containing acetic acid; (iii) loading a *Taxus* extract mixture or semi-synthetic or total synthetic reaction mixture onto the column; (iv) eluting the mixture with an organic solvent, preferably acetone/acetic acid; (v) collecting the eluate into one or more fractions; (iv) confirming the presence of the desired taxane in the one or more fractions; and (iv) purifying the desired taxane by crystallization.

In accordance with one alternative embodiment, the taxane containing material is subjected to normal phase liquid chromatography ("NPLC") in order to purify the taxol and other taxanes contained in a crude or semi-purified extract. Several variables are usually examined to achieve separation and purification by liquid chromatography, including column packing (e.g., stationary phase or absorbent), composition of an eluant (e.g., mobile phase), column dimension, and eluant flow rate. These variables are known to those skilled in the art or can be readily determined without undue experimentation.

The chromatographic column dimensions, as well as the temperature, flow rates, and time of chromatographic separations are not critical to the practice of this invention, and are based primarily upon the requirements for efficient chromatography which are known to those of skill in the art or can be readily determined without undue experimentation.

In one alternative embodiment, chromatographic purification of semi-synthetic paclitaxel may be effected on DEAM resin (20 μm spherical, 100 Å) using ethyl acetate with 0.5% acetic acid as the mobile phase. The progress of the separation may be monitored by UV absorbance at an appropriate absorbing wave length, preferably 254 nm and 280 nm. The paclitaxel peak is collected in fractions. The ascending portion (from baseline to apex) of the peak can be collected in several fractions, typically 2 or 3. The earliest of these fractions will contain most of the 7-epi-taxol and 10-deacetyl-7-epi-taxol impurities. The remaining portion of the peak may be collected in one or-more fractions. A step-gradient of a 50:50 mixture of methanol and ethyl acetate with 0.5% acetic acid may be employed to elute 10-deacetyltaxol from the column.

In one alternative embodiment, step gradient elution of the remaining impurities is preferred over use of a linear gradient for brevity and ease of operation. A more complex equipment set is required to make use of a linear gradient. Step gradient elution, using a pre-mixed solvent system, may be accomplished by changing a single valve supplying the mobile phase to the pump. In another alternative embodiment, it is preferred to delay introduction of methanol into the mobile phase system because small amounts of methanol speed the elution of a late eluting impurity, such 2-debenzoyltaxal, for example.

In one alternative embodiment, the liquid chromatography systems of the present invention are preferentially used in a preparative mode (greater than 100 mg quantities). Preparative columns are typically 7 mm to 300 mm in diameter and 10 cm to 100 cm in length. Those skilled in the art of chromatography can easily select a column with bed dimensions appropriate to the amounts of material being purified. Flow rates of the mobile phase are adjusted according to various factors including column dimensions, particle size and pore size of the resin, and desired peak resolution. Typical flow rates for preparative columns may range from 10 ml/minute to 4l/minute.

The times required for chromatographic runs range from about 10 minutes to about 30 hours. Temperatures for chromatographic separation are typically at ambient temperature, although slightly higher temperatures can be used.

When practicing the chromatographic separation according to the present invention, the column may be operated in low-pressure (LPLC) to medium-pressure (NIPLC) modes, typically 10 to 500 p.s.i.g. It may also be run in high-pressure (HPLC) mode, typically 500 to 2000 p.s.i.g.

In another embodiment, the *Taxus* extract mixture or semi-synthetic or total synthetic reaction mixture may be dissolved prior to loading onto the column. For example, the mixture may be dissolved using an organic solvent, or by other means known to those having ordinary skills in the art. A preferred organic solvent mixture comprises acetone/acetic acid. The dissolved mixture may then be loaded onto a column packed with an appropriate amount of PBS resin.

Solvents (eluants) useful in this invention may be selected by reference to the standard practices of chromatography. Typically, a moderately polar organic solvent such as acetone, ethyl acetate, tetrahydrofuran, or acetonitrile may be used as eluant. Other ketones, ethers, and esters containing 1-5 carbons may be used as well. Modifiers to the eluant may include more polar solvents such as lower alcohols, acetic acid, and water if the mixture contains more polar taxanes, as well as less polar organic solvents such as alkanes and halogenated hydrocarbons if the mixture contains less polar taxanes. The percentages of the modifiers may be 0-100% depending on the nature of the mixture to be purified. This percentage can be readily determined by those skilled in the art.

In another embodiment, the *Taxus* extract mixture or crude reaction mixture may be dissolved in an organic solvent comprising ethyl acetate/THF to form a taxane solution. The taxane solution may be stirred with mild heating, and then vacuum filtered to remove impurities and debris therefrom.

The crude taxane solution may also be diluted in an organic solvent, preferably a EtOAc/THF solution. The solution may be injected and/or loaded onto a column containing an appropriate amount of PBS resin. Beforehand, the column may be equilibrated with-an organic solvent, preferably EtOAc/acetic acid. After the taxane solution is injected/loaded onto the column, EtOAc may be injected into the column. The eluted material may be collected in multiple fractions. A step gradient comprising a methanol/EtOAc mixer solvent may be employed. The desired taxane is eluted from the column, and then collected in one or more fractions. A wash step may be employed.

In some cases it may be advantageous to employ a gradient solvent system, either step gradient or continuous gradient. The concentration limits of the gradients are determined by: (1) the concentration of organic solvent necessary to elute taxanes from the absorbent; and (2) the requirement that the organic solvent be completely miscible and exist in a single phase at the concentration required to elute the taxanes. For instance, 100% ethyl acetate may be used initially, then switching to 1-10% methanol in a single step, multiple step, or continuous gradient fashion. This system may be necessary to separate various taxanes that differ substantially in polarity and is readily determined by those skilled in the art.

The presence of the desired taxane in the one or more fractions may be detected using analytical techniques known in the art such as thin layer chromatography (TLC), infrared (IR) spectroscopy, nuclear magnetic resonance (NMR) spectroscopy, high performance liquid chromatography (HPLC), reversed phase HPLC, and mass spectrometry (MS). After the desired taxane(s) is collected from the column, it may be further purified using other chromatographic methods, or crystallization and/or one or more recrystallizations, depending on the desired purity of the end product taxane molecule or taxane mixture. Crystallization and recrystallization may be conducted using a binary or ternary solvent system, i.e., at least one solubilizing solvent and at least one anti-solvent. Examples of solubilizing solvents include, among others, acetone, methyl-tert-butyl ether, methylene chloride, THF, methanol, ethanol, isopropyl alcohol, and acetonitrile. Examples of anti-solvents include hydrocarbon solvents such as hexane and heptane, as well as water. In most cases, the solubilizing solvent and the anti-solvent are miscible in the ratios used. Examples of solvent systems useful with taxane molecules include, among others, acetone/hexane and methanol/water.

FIGS. 1 and 2 show an exemplary chemical reaction scheme using a PBS resin (e.g, DEAM), of the present invention. Specifically, it shows a semi-synthetic process of converting a taxane amide to paclitaxel or other taxanes, and purifying the taxane from the reaction product using a PBS resin. Methods of converting a taxane amide to paclitaxel or other taxanes are shown in the patent applications previously stated herein.

Having described specific chromatographic techniques and conditions suitable for this invention, a preferred embodiment of the isolation, separation, and purification of the taxane derivatives in accordance with this invention is described below.

EXAMPLES

The following examples are included for illustrative purposes only and are not intended to limit the scope of the invention to any particular step or ingredient, for example.

Example 1

This example shows the use of PEI Resin in the Purification of taxol A (Paclitaxel) and taxol B (Cephalomannine) from semi-purified *Taxus media* Densiformis extract. Here, a 75 liter column was packed with 24.5 Kg of J. T. Baker PEI resin (40 micron particle size, 275 angstrom pore size, J. T. Baker Item #7264). The resin was equilibrated with 2 column volumes, 150 liters, of acetone containing 0.5% acetic acid at a flow rate of 3.2 liters/min. The semi-purified *Taxus* extract feed was then loaded onto the column at a concentration of about 250 mg/mL in acetone and at a rate of 0.5 liters/min. The concentration of taxol was 2.5 weight % or 2.5 grams of feed solid for 100 grams of PEI resin. The weight percent of taxol A and taxol B in the feed solid was 10.8 weight %. The feed was eluted with acetone containing 0.5% acetic acid at a flow rate of 3.2 liters/min (superficial velocity=4.4 cm/min.). A total of 10 fractions were collected. Fraction 1 and fraction 10 were 75 liters each (1 column volume) and fractions 2-9 were 19 liters each (1/4 column volume). Product fractions 2-5 contained 87.96% of the total taxol A & B in the feed and the weight percentage of the combined product fractions was 58.59 weight %. This product was adequate for further purification via crystallization.

Example 2

Figure 3:
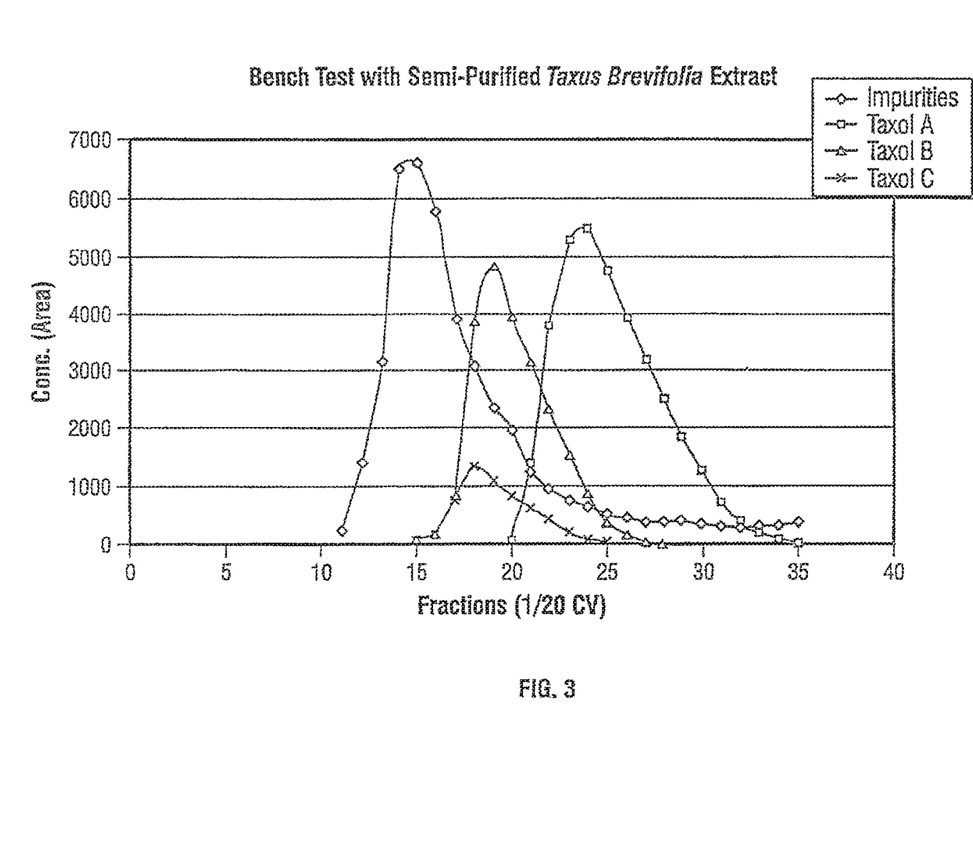
FIG. 3 shows separation of taxol A from taxol, B, C and other impurities using a PEI resin of the present invention.

This example shows the use, of PEI Resin in the Purification of taxol A (Paclitaxel), taxol B (Cephalomannine), and taxol C from impurities found in semi-purified *Taxus brevifolia* extract. Here, solid feed of semi-purified *Taxus brevifolia* extract was dissolved in acetone containing 0.6% acetic acid. This solution was loaded onto J. T. Baker PEI resin (40 micron particle size, 275 angstrom pore size, J. T. Baker Item #7264). The feed load was 3% or 3 grams of feed solid for 100 grams of PEI resin. The elution solvent was acetone containing 0.6% acetic acid. As the feed components were eluted from the column, samples were collected approximately every 1/20th of a column volume. These fractions were analyzed by HPLC and the data was plotted as shown in FIG. 3. This run shows the separation of the impurities from taxol A, B, and C.

Example 3

This example illustrates the use of DEAM resin in the purification of crude semisynthetic taxol A (Paclitaxel). Here, the molecules used as reactants in the semi-synthetic or total synthetic process were derived from a *Taxus* plant, excluding *Taxus brevifolia*. In this example, the instrument used was a NovaPrep 200 Preparative High Performance Liquid Chromatography System combined with a Hitachi L-7400 UV detector set to a wavelength of 254 nm. Both of these units are directly connected to a PC interface which runs the LC ReSponder controller software—Version 2.11.V (R & S Technology, Inc.).

The column is a Load & Lock 2 Preparative LC column (R & S Technologies, Inc./Varian) which has the following dimensions: Inner Diameter=5 cm; Length=25 cm; Volume=490.87 cm$^3$ The column is packed with Diethylaminomethyl (DEAN) Bonded Silica Gel: Spherical, 20 micron particle size, 120 angstrom average pore size. The column is packed with 270 g of resin compressed to 800 psi.

A total of 7.1 grams of crude taxol A was prepared via the primary amine conversion chemistry described in U.S. Serial Appl. No. PCT/US03/10557 entitled "Conversion of Taxane Molecules." The crude taxol was dissolved using about 35 mL of solvent comprising of 90% (vol.) ethyl acetate/10% (vol.) tetrahydrofuran. The solution was stirred with mild heating (~35-40° C.) for 30 minutes. The clear solution was vacuum filtered to remove any small fibers or particulates before injection. After filtration, the solution was transferred to a graduated cylinder and diluted to a final volume of 42.5 mL (6× dilution) using the 90:10 EtOAc/T/HF solution. It was then remixed to ensure uniformity before sampling. The loading for this run was 2.625% or 2.625 grams of feed solids for 100 grams of DEAM resin. The flow rate was set at 90 mL/minute. The column was equilibrated for a period of 20 minutes with the standard mobile phase consisting of EtOAc+0.5% acetic acid (v/v). At the 20-minute mark, the entire volume of the previously prepared sample solution was injected on the column immediately followed by a 20 mL injection line flush with EtOAc. The fractions were collected in the following manner (all times listed are from injection point—time 0):

TABLE 1

| Fraction | Open | Close | Total Time | Area % Pac | Mass of Pac(mg) |
|---|---|---|---|---|---|
| 1 | 6:15 | 15:00 | 8:45 | 10.73 | 12.2 |
| 2 | 15:00 | 15:15 | 0:15 | 74.95 | 96.4 |
| 3 | 15:15 | 16:30 | 1:15 | 95.43' | 995.0 |
| 4 | 16:30 | 29:00 | 12:30 | 99.25 | 4284.6 |
| 5 | 29:00 | 35:15 | 6:15 | 100.0 | 555.3 |
| | | | | TOTAL | 5943.4 mg |

Figure 4:
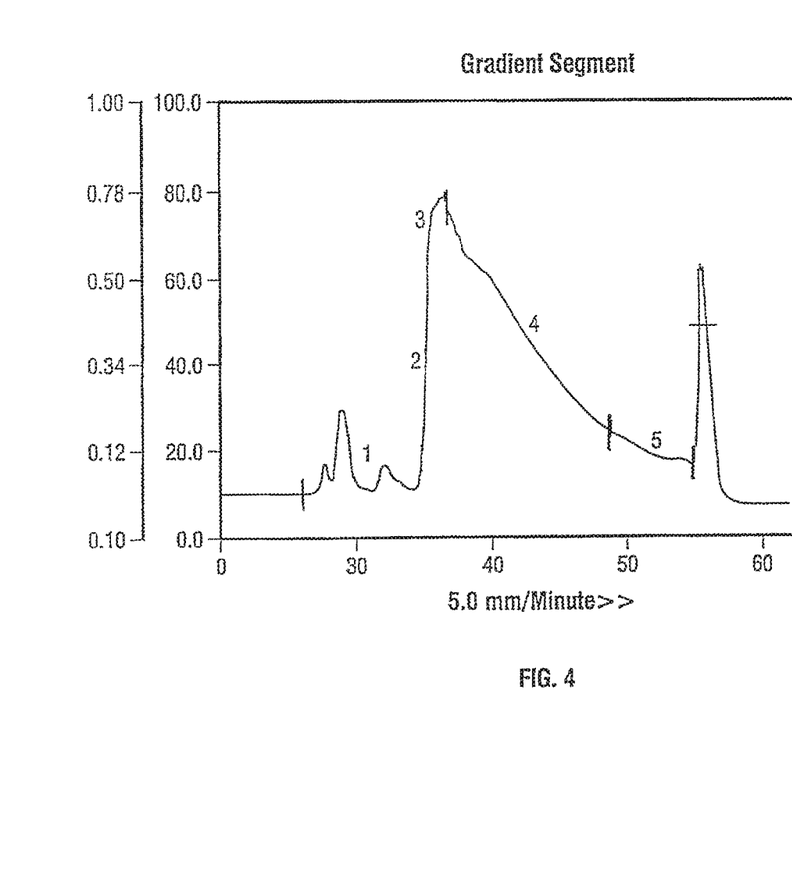
FIG. 4 shows separation of semi-synthetic taxol A from other taxane by-products using a DEAM resin of the present invention.

A 50% stop gradient was started at the 29 minute mark (i.e. from injection point—time 0) consisting of a 50:50 methanol/ethyl acetate wash solvent mobile phase. This was run for 20 minutes total at which point the run was complete. This wash step allows for faster elution of the 110-Deacetyltaxol A compound that elutes after taxol A. The last fraction collection valve (i.e. fraction 5) was closed as soon as the UV detector registered a rapid increase in absorbance, which indicates elution of the 10-Deacetyltaxol A. All of the 1 ODeacetyltaxol A flushes from the column under the above condition within 10 minutes. However, to ensure the column has been purged of any residual material and as a regular practice, the wash step is always a full 20 minutes in length. Thus, the entire run from the point of injection through the complete column wash step was 49 minutes. A trace of the chromatogram showing the collection points of fractions 1-5 is shown in FIG. 4.

Fractions 3, 4, and 5 were combined in the pass pool for subsequent crystallization work. The fraction analysis (by HPLC) of the passing fractions gives a total of 5.835 g of taxol A. Dividing by the total mass of taxol in all fractions, the recovery is calculated to be 98.18%. The purity of the crude material going onto the column was 87.9 wt. % taxol, and after column purification, the purity of the passing combined fractions was 98.71% area (by HPLC) taxol A.

Example 4

A 44 liter column was packed with 10 kg of J. T. Baker PEI resin (40 micron particle size, 275 angstrom pore size). The resin was equilibrated with 3 column volumes, 135 liters, of 50 v %/50 v % ethyl acetate and heptane containing 0.5% acetic acid at a flow rate of 1.0 liter/min. The flow rate for the remaining fractions was at 1.0 liter/min. The semi-purified food (derived from *Taxus media* 'Runyan') was loaded onto the column at a concentration of 250 mg/ml in ethyl acetate. The primary taxanes purity of the feed is 57 wt %. First, the first fraction was 170 liters of 50 v %/50 v % ethyl acetate and heptane containing 0.5 v % acetic acid. Second, three 10-liter fractions of 50 v %/50 v % ethyl acetate and heptane containing 0.5% acetic acid was collected. Third, the product fraction was 90 liters of 90 v %/10 v % ethyl acetate and methanol. Lastly, the column was wash with 45 liters of 90 v %/10 v % ethyl acetate/methanol. The product pool contains 93.5 wt % primary taxanes. The percent recovery of taxol A and B was 95%.

Throughout the description, where the present invention is described as having, including, or comprising specific components, or where processes are described as having, including, or comprising specific process steps, it is contemplated that the present invention also consists essentially of, or consists of, the recited components or processing steps. Further, it should be understood that the order of steps or order for performing certain actions are immaterial so long as the invention remains operable. Moreover, two or more steps or actions may be conducted simultaneously so long as the invention remains operable. Also, one or more steps or elements may be omitted from the claimed invention, or the invention described herein suitably may be practiced in the absence of any component or step which is not specifically disclosed herein, so long as the invention remains operable.

Further, the present invention may be embodied in other specific forms without departing from the spirit or essential characteristics thereof. The foregoing embodiments are therefore to be considered illustrative rather than limiting the invention described herein.

The content or each patent and non-patent document referred to herein is expressly incorporated herein by reference in its entirety.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method of crystallizing docetaxel comprising:
   (a) combining docetaxel and at least one solubilizing solvent to obtain a solution, wherein the solubilizing solvent is methylene chloride; and
   (b) adding an anti-solvent to the solution to obtain a crystalline docetaxel, wherein the anti-solvent is water.

2. The method of claim 1, further comprising recrystallizing the crystalline docetaxel.

3. The method of claim 2, wherein the recrystallization comprises:
   (c) combining the crystalline docetaxel and a solubilizing solvent to obtain a second solution; and
   (d) adding an anti-solvent to the second solution.

4. The method of claim 1, wherein the docetaxel used in step (a) is isolated from a taxane material comprising docetaxel obtained from a semi-synthesis or total synthesis process, the isolation process comprising:
   loading or injecting the material on a column comprising a polyethyleneimine-bonded silica (PBS resin;
   (ii) eluting docetaxel from the PBS resin; and
   (iii) recovering the eluted docetaxel.

5. The method of claim 4, wherein molecules used as reactants in the semi-synthetic or total synthetic process are not derived solely from *Taxus brevifolia*.

6. The method of claim 4, wherein the material loaded or injected on the column comprises less than about 8% by weight of C-2' benzoyl primary taxanes.

7. The method of claim 4, wherein the PBS resin is diethylaminomethyl (DEAM).

8. The method of claim 4, wherein the PBS resin is polyethyleneimine (PEI).

9. The method of claim 8, wherein the amino groups of the PEI are functionalized.

10. The method of claim 4, wherein the PBS resin has an average pore size ranging from about 60 to about 800 Angstrom Units and an average particle size ranging from about 0.25 to about 500 microns.

* * * * *

UNITED STATES PATENT AND TRADEMARK OFFICE
CERTIFICATE OF CORRECTION

PATENT NO. : 9,527,825 B2  
APPLICATION NO. : 15/053793  
DATED : December 27, 2016  
INVENTOR(S) : Brian A. Bucher et al.

Page 1 of 1

It is certified that error appears in the above-identified patent and that said Letters Patent is hereby corrected as shown below:

In the Claims

Claim 4, Column 18, Line 32:

Insert -- (i) -- before "loading or injecting the..."

Claim 4, Column 18, Line 33:

Delete "silica (PBS" and replace with -- silica (PBS) --.

Signed and Sealed this  
Twenty-first Day of March, 2017

Michelle K. Lee  
*Director of the United States Patent and Trademark Office*